US011617714B2

(12) United States Patent
Olynyk

(10) Patent No.: US 11,617,714 B2
(45) Date of Patent: Apr. 4, 2023

(54) SUBLINGUAL THERAPEUTIC SOLUTIONS AND METHODS

(71) Applicant: Jeffrey R Olynyk, Parkland, FL (US)

(72) Inventor: Jeffrey R Olynyk, Parkland, FL (US)

( * ) Notice: Subject to any disclaimer, the term of this patent is extended or adjusted under 35 U.S.C. 154(b) by 320 days.

(21) Appl. No.: 17/068,449

(22) Filed: Oct. 12, 2020

(65) Prior Publication Data

US 2021/0022992 A1    Jan. 28, 2021

Related U.S. Application Data

(63) Continuation of application No. 16/667,007, filed on Oct. 29, 2019, now Pat. No. 10,799,452, which is a
(Continued)

(51) Int. Cl.
*A61K 36/00* (2006.01)
*A61K 9/00* (2006.01)
(Continued)

(52) U.S. Cl.
CPC ............... *A61K 9/006* (2013.01); *A61K 9/08* (2013.01); *A61K 31/194* (2013.01); *A61K 31/352* (2013.01); *A61K 31/404* (2013.01); *A61K 31/5685* (2013.01); *A61K 36/07* (2013.01); *A61K 36/185* (2013.01);
(Continued)

(58) Field of Classification Search
CPC .................................................... A61K 36/00
See application file for complete search history.

(56) References Cited

U.S. PATENT DOCUMENTS 6,376,549 B1    4/2002  Fine
2006/0009413 A1    1/2006  Frey, II
(Continued)

OTHER PUBLICATIONS

Bioactive Food as Dietary Interventions for Diabetes, Eds. R.R. Watson and V.R. Preedy, Jaffe, Chap. 30, Phytonutrients in Diabetes Management, pp. 339, 345, 347-349, Academic Press, San Diego, 2013.*

(Continued)

*Primary Examiner* — Rosanne Kosson
(74) *Attorney, Agent, or Firm* — Guy Cumberbatch

(57) ABSTRACT

Supplement formulations of estrogen blocker, glycogen manager, and muscle recovery solutions and sublingual therapies for increasing absorption rates thereof. The sublingual delivery systems allow the body to absorb up to 94.9% of each dose directly into the bloodstream, completely bypassing the digestion process. Sublingual delivery (under the tongue) results in potencies 4 to 5 times greater than most capsules and powders. An estrogen blocker solution includes purified water, vegetable glycerin, polypropylene glycol, potassium benzoate, citric acid, calcium D glucarate, 7 keto DHEA, IO3, DIM, nettle root extract, agaricus biporus extract, narigin extract, and quercetin dehydrate. Formulas for glycogen manager, and muscle recovery are also disclosed. The glycogen manager formula includes the effective ingredients phellodendron extract, Banaba extract, Vanadium, and Chromium. A method of use involves taking one or two droppers (1 or 2 ml) of the solution sublingually for 30 seconds, and then swallowing.

14 Claims, 6 Drawing Sheets

| No. # | Ea. Unit Contains | Units | Location | Raw Mat No. | INGREDIENTS | Lot No. | Theoretical Weight |
|---|---|---|---|---|---|---|---|
| 1 | 0.10 | mg | | | CHROMIUM (AMINO ACID CHELATE) | | 0.0001 |
| 2 | 5.00 | mg | | | VANADIUM (VANADIUM SULFATE) | | 0.005 |
| 3 | 225.00 | mg | | | PHELLODENDRON EXTRACT | | 0.225 |
| 4 | 150.00 | mg | | | BANABA EXTRACT | | 0.150 |
| 5 | 1000.00 | mg | | | PURIFIED WATER | | 1.000 |
| 6 | 200.00 | mg | | | VEGETABLE GLYCERIN | | 0.200 |
| 7 | 200.00 | mg | | | POLYPROPYLENE GLYCOL | | 0.200 |
| 8 | 200.00 | mg | | | NATURAL & ARTIFICIAL FLAVOR | | 0.200 |
| 9 | 5.00 | mg | | | POTASSIUM BENZOATE | | 0.005 |
| 10 | 15.00 | mg | | | CITRIC ACID | | 0.015 |

GLYCO MANAGER INGREDIENTS

Related U.S. Application Data continuation of application No. 15/479,081, filed on Apr. 4, 2017, now Pat. No. 10,471,007.

(60) Provisional application No. 62/435,623, filed on Dec. 16, 2016.

(51) Int. Cl.
  *A61K 31/194*      (2006.01)
  *A61K 31/5685*     (2006.01)
  *A61K 31/404*      (2006.01)
  *A61K 36/185*      (2006.01)
  *A61K 36/07*       (2006.01)
  *A61K 36/752*      (2006.01)
  *A61K 31/352*      (2006.01)
  *A61K 47/10*       (2017.01)
  *A61K 47/12*       (2006.01)
  *A61K 9/08*        (2006.01)

(52) U.S. Cl.
  CPC ............ *A61K 36/752* (2013.01); *A61K 47/10* (2013.01); *A61K 47/12* (2013.01)

(56) References Cited

U.S. PATENT DOCUMENTS

2010/0227001 A1    9/2010  Demeter
2017/0037043 A1*   2/2017  Liu .................... C07D 455/03

OTHER PUBLICATIONS

Angstrom Minerals, website, https://phpure.com/angstrom-minerals, printed Nov. 16, 2016.
A Blend of Phellodendron and Crape Myrtle Improves Glucose Tolerance in Exercise-Trained Men, Canale, et al., Nutrition and Metabolic Insights, 2011:4 39-47.
Metabolic effects of vanadyl sulfate in humans with non-insulin-dependent diabetes mellitus: In vivo and in vitro studies, Goldfine, et al., Metabolism—Clinical and Experimental, vol. 49, Issue 3, pp. 400-410, Mar. 2000.
Sublingual Chromium Picolinate Solution, website ad, http://www.goodearthnaturalfoods.com/shop/product, printed Nov. 16, 2016.
Sublingual Ionic Vanadium, website ad, http://www.naturesremediesctr.com/product/1012, printed Nov. 16, 2016.
Angstrom Liquid VCZ drops, website ad, http://www.healthshop101.com/vcz.html, printed Nov. 16, 2016.
Vanadium with Chromium, 180 Tablets, website ad, https://www.amazon.com/Source-Naturals-Vanadium-Chromium-Tablets/dp/B004FHFS, printed Nov. 16, 2016.

* cited by examiner

| No. # | Eq. Unit Contains | Unit | Location | Raw Mat No. | INGREDIENTS | Lot No. | Theoretical Weight |
|---|---|---|---|---|---|---|---|
| 1 | 300.00 | mg | | | CALCIUM D GLUCARATE | | 0.300 |
| 2 | 200.00 | mg | | | 7 KETO DHEA (7-KETODEHYDROEPIANDROSTERONE) | | 0.200 |
| 3 | 100.00 | mg | | | ICOLE 3 CARBINOL (I3C) | | 0.100 |
| 4 | 100.00 | mg | | | DIINDOYLMETHANE (DIM) | | 0.100 |
| 5 | 50.00 | mg | | | NETTLE ROOT EXTRACT | | 0.050 |
| 6 | 25.00 | mg | | | AGARICUS BIPORUS EXTRACT | | 0.025 |
| 7 | 25.00 | mg | | | NARIGIN EXTRACT | | 0.025 |
| 8 | 10.00 | mg | | | QUERCETIN DIHYDRATE | | 0.010 |
| 9 | 283.00 | mg | | | PURIFIED WATER | | 0.283 |
| 10 | 50.00 | mg | | | VEGETABLE GLYCERIN | | 0.050 |
| 11 | 50.00 | mg | | | POLYPROPYLENE GLYCOL | | 0.050 |
| 12 | 0.10 | mg | | | NATURAL & ARTIFICIAL FLAVOR | | 0.000 |
| 13 | 2.00 | mg | | | POTASSIUM BENZOATE | | 0.002 |
| 14 | 5.00 | mg | | | CITRIC ACID | | 0.005 |

FIG. 1A – ESTROGEN BLOCKER INGREDIENTS

| TEST | SPECIFICATIONS | | | METHOD | RESULTS |
|---|---|---|---|---|---|
| Description | Clear solution | | | Visual | Conform |
| Serving Size | 1 mL (1 droppers) | | | As per label | Conform |
| Serving Per Container | 60 | | | As per label | Conform |
| Ingredients | Label Claim | Unit | Result | METHOD | % Label Claim |
| CALCIUM D GLUCARATE | 300.0 | mg | 300.0 | USP/NF CURRENT <ATOMIC ABSORPTION> | 100.0 |
| 7 KETO DHEA (7-KETOH-HYDROEPIANDROSTERONE) | 200.0 | mg | * | | * |
| INDOLE 3 CARBINOL (I3C) | 100.0 | mg | * | | * |
| DIINDOYLMETHANE (DIM) | 100.0 | mg | * | | * |
| NETTLE ROOT EXTRACT | 50.0 | mg | * | | * |
| AGARICUS BIPORUS EXTRACT | 25.0 | mg | * | | * |
| NARIGIN EXTRACT | 25.0 | mg | * | | * |
| QUERCETIN DIHYDRATE | 10.0 | mg | * | | * |
| Microbiology: | | | | | |
| Total plate count | <10000 cfu/g | | | USP/NF Current | <10000 cfu/g |
| E Coli | Negative 10 g | | | USP/NF Current | Negative |
| Yeast and Mold | <1000 cfu/g | | | USP/NF Current | <1000 cfu/g |
| Salmonella | Negative 25g | | | USP/NF Current | Negative |

Excipients: Purified Water, Vegetable Glycerin, Polypropylene glycol, Natural & Artificial Flavor, Potassium Benzoate, and Citric Acid.

* BY INPUT

FIG. 1B - ESTROGEN BLOCKER ANALYSIS

| No. # | Ea. Unit Contains | Units | Location | Raw Mat No. | INGREDIENTS | Lot No. | Theoretical Weight |
|---|---|---|---|---|---|---|---|
| 1 | 0.10 | mg | | | CHROMIUM (AMINO ACID CHELATE) | | 0.0001 |
| 2 | 5.00 | mg | | | VANADIUM (VANADIUM SULFATE) | | 0.005 |
| 3 | 225.00 | mg | | | PHELLODENDRON EXTRACT | | 0.225 |
| 4 | 150.00 | mg | | | BANABA EXTRACT | | 0.150 |
| 5 | 1000.00 | mg | | | PURIFIED WATER | | 1.000 |
| 6 | 200.00 | mg | | | VEGETABLE GLYCERIN | | 0.200 |
| 7 | 200.00 | mg | | | POLYPROPYLENE GLYCOL | | 0.200 |
| 8 | 200.00 | mg | | | NATURAL & ARTIFICIAL FLAVOR | | 0.200 |
| 9 | 5.00 | mg | | | POTASSIUM BENZOATE | | 0.005 |
| 10 | 15.00 | mg | | | CITRIC ACID | | 0.015 |

FIG. 2A - GLYCO MANAGER INGREDIENTS

| TEST | SPECIFICATIONS | | | | METHOD | RESULTS |
|---|---|---|---|---|---|---|
| Description | Clear solution | | | | Visual | Conform |
| Serving Size | 2 mL (2 droppers) | | | | As per label | Conform |
| Serving Per Container | 30 | | | | As per label | Conform |
| Ingredients | Label Claim | Unit | Result | | METHOD | % Label Claim |
| CHROMIUM(AMINO ACID CHELATE) | 0.1 | mg | 0.1 | | USP/NF CURRENT <ATOMIC ABSORPTION> | 100.0 |
| VANADIUM (VANADIUM SULFATE) | 5.0 | mg | * | | * | * |
| PHELLODENDRON EXTRACT | 225.0 | mg | * | | | * |
| BANABA EXTRACT | 150.0 | mg | * | | | * |
| Microbiology: | | | | | | |
| Total plate count | <1000 cfu/g | | | | USP/NF Current | <10000 cfu/g |
| E Coli | Negative 10 g | | | | USP/NF Current | Negative |
| Yeast and Mold | <1000 cfu/g | | | | USP/NF Current | <1000 cfu/g |
| Salmonella | Negative 25g | | | | USP/NF Current | Negative |

Excipients: Purified Water, Vegetable Glycerin, Polypropylene glycol, Natural & Artificial Flavor, Potassium Benzoate, and Citric Acid.

* BY INPUT

FIG. 2B - GLYCO MANAGER ANALYSIS

| No. # | Ea. Unit Contains | Units | Location | Raw Mat No. | INGREDIENTS | Lot No. | Theoretical Weight |
|---|---|---|---|---|---|---|---|
| 1 | 500.00 | mg | | | L-LEUCINE | | 0.500 |
| 2 | 250.00 | mg | | | L-ISOLEUCINE | | 0.250 |
| 3 | 250.00 | mg | | | L-VALINE | | 0.250 |
| 4 | 300.00 | mg | | | PURIFIED WATER | | 0.300 |
| 5 | 100.00 | mg | | | VEGETABLE GLYCERIN | | 0.100 |
| 6 | 100.00 | mg | | | POLYPROPYLENE GLYCOL | | 0.100 |
| 7 | 0.20 | mg | | | NATURAL & ARTIFICIAL FLAVOR | | 0.0002 |
| 8 | 2.00 | mg | | | POTASSIUM BENZOATE | | 0.002 |
| 9 | 5.00 | mg | | | CITRIC ACID | | 0.005 |

FIG. 3A – MUSCLE RECOVERY INGREDIENTS

| TEST | SPECIFICATIONS | | | METHOD | RESULTS |
|---|---|---|---|---|---|
| Description | Clear solution | | | Visual | Conform |
| Serving Size | 1 mL (1 droppers) | | | As per label | Conform |
| Serving Per Container | 60 | | | As per label | Conform |
| Ingredients | Label Claim | Unit | Result | METHOD | % Label Claim |
| L-LEUCINE | 500.0 | mg | 500.0 | HPLC (IN HOUSE METHOD) | 100.0 |
| L-ISOLEUCINE | 250.0 | mg | 250.0 | | 100.0 |
| L-VALINE | 250.0 | mg | 250.0 | | 100.0 |
| Microbiology: | | | | | |
| Total plate count | <1000 cfu/g | | | USP/NF Current | <10000 cfu/g |
| E Coli | Negative 10 g | | | USP/NF Current | Negative |
| Yeast and Mold | <1000 cfu/g | | | USP/NF Current | <1000 cfu/g |
| Salmonella | Negative 25g | | | USP/NF Current | Negative |

Excipients: Purified Water, Vegetable Glycerin, Polypropylene glycol, Natural & Artificial Flavor, Potassium Benzoate, and Citric Acid.

FIG. 3B - MUSCLE RECOVERY ANALYSIS

SUBLINGUAL THERAPEUTIC SOLUTIONS AND METHODS

RELATED APPLICATIONS

The present application is a continuation of U.S. application Ser. No. 16/667,007, filed Oct. 29, 2019 and now issued as U.S. Pat. No. 10,799,452, which is a continuation of U.S. application Ser. No. 15/479,081, filed Apr. 4, 2017 and now issued as U.S. Pat. No. 10,471,007, which claims priority under 35 U.S.C. 119 to U.S. Provisional application No. 62/435,623, filed Dec. 16, 2016, the disclosure of which is incorporated by reference herein.

FIELD OF THE INVENTION

The present invention relates generally to supplements and methods of ingestion and, in particular, to supplement formulations of estrogen blocker, glycogen manager, and muscle recovery solutions and sublingual therapies for increasing absorption rates thereof.

BACKGROUND OF THE INVENTION

Numerous orally-ingested physiological supplement products on the marketplace have a relatively low rate of absorption, drastically diminishing their effectiveness. That is, most powders and pills are broken down during the digestion process, preventing key ingredients from reaching the bloodstream. Total absorption rates for many commercial supplements are as low as 10%, meaning that up to 90% of their key ingredients never perform their desired function.

Despite a huge number of vendors in the supplement marketplace, there is a need for products that have increased absorption rates.

SUMMARY OF THE INVENTION

The present application describes techniques and supplement formulations for subliminal therapies to increase nutrient absorption. The disclosed sublingual delivery system allows the body to absorb an astounding 94.9% of each dose directly into the bloodstream, completely bypassing the digestion process. Sublingual delivery (under the tongue) results in potencies 4 to 5 times greater than most capsules and powders.

BRIEF DESCRIPTION OF THE DRAWINGS

Features and advantages of the present invention will become appreciated as the same become better understood with reference to the specification, claims, and appended drawings wherein:

FIG. 1A is a table showing exemplary ingredients combined to form an estrogen blocker solution intended for sublingual delivery;

FIG. 1B is a table showing a chemical analysis of the exemplary estrogen blocker solution derived from the ingredients of FIG. 1A;

FIG. 2A is a table showing exemplary ingredients combined to form a muscle recovery solution intended for sublingual delivery;

FIG. 2B is a table showing a chemical analysis of an exemplary muscle recovery solution derived from the ingredients of FIG. 2A;

FIG. 3A is a table showing exemplary ingredients combined to form a glycogen manager solution intended for sublingual delivery; and FIG. 3B is a table showing a chemical analysis of an exemplary glycogen manager solution derived from the ingredients of FIG. 3A.

DETAILED DESCRIPTION OF THE PREFERRED EMBODIMENTS

The present invention provides a number of preferred formulations of liquid supplements, and methods of sublingual therapeutic ingestion. Although some of the ingredients of the formulations are considered useful for the stated applications, it is not believe that they have been combined in the particular manners disclosed herein. That said, the specific compositions of the formulations, in particular the proportions of ingredients, is not considered to be exacting, and slight variations of up to 20% of any one ingredient is believed also to be efficacious.

Estrogen Blocker Solution

The estrogen blocker is a premium matrix of natural earth elements and compounds that can eradicate, decrease and in some cases even stop the synthesis of estrogen, while simultaneously increasing and supporting maximum testosterone levels. To ensure effectiveness, the estrogen blocker was developed for sublingual delivery (under the tongue) for maximum absorption.

Testosterone and Estrogen are present, and both play vital roles, in both men and women. The science community, through extensive research, has made it increasingly clear that estrogen directly impacts testosterone just as testosterone directly impacts estrogen. When estrogen levels are too high they have the ability to decrease the levels of testosterone. This means that estrogen levels have everything to do with the amount of testosterone that can be effective within the body; estrogen levels alone can inhibit testosterone by affecting the ratio of the two combined.

Removing the negative effects of increased estrogen in males, certain compounds have been presented in numerous peer-reviewed medical journals to do just that. Compounds such as: Indole-3-carbinol (I3C) cause growth arrest, increased cell death and ameliorate the effects of estrogen; Diindolylmethane (DIM), much like I3C, it is found in cruciferous vegetables and has the ability to arrest estrogen activity and assist in its metabolism; Agaricus Bisporus, found in mushrooms, has very powerful anti-aromatase activity which suppresses estrogen bio-synthesis; Calcium D Glucarate, initiates a process called glucaronidation, the process by which estrogen is metabolized and detoxified from the body. These, along with other compounds used in Premier Pharmaceuticals powerful and effective proprietary *Estrogen Blocker*, have very strong effects on lowering negative and unwanted estrogen levels. By not only removing them from the body but also by stopping or decreasing the amount of testosterone that is converted into estrogen and estrogen metabolites by a process called aromatization. After years of research, the applicant has obtained only the best quality ingredients to formulate these compounds into one product to make it easy for men to keep their hormone levels normalized and their estrogen production at bay.

Furthermore, the overproduction of certain sex hormones is intimately related to the synthesis of cancer. Cancer rates are continuously growing, and are said to affect 1 out of 2 people in their lifetimes. Studies show that the compounds used in the estrogen blocker solution also possess the chemoprotective properties found in numerous studies to regress cancers and tumors in patients by lowering bad hormone levels and balancing and regulating the good ones; so it could be said that these compounds can be used as a means of prevention and not just treatment, for the reduction and prevention of cancers and not just the removal and lowering of unwanted sex hormones in the athlete or healthy individual.

FIG. 1A shows a table of ingredients used to form an estrogen blocker solution. The actual milligrams of each of the components for an exemplary batch are given, along with their theoretical weight. The total batch size is 60 L.

An exemplary procedure for forming the estrogen blocker solution first involves adding purified water into a large capacity compounding tank including a mixer with nitrogen bubbling until the end of the process. Next, ingredients #10-11 and #13-14 (vegetable glycerin, polypropylene glycol, potassium benzoate, and citric acid) are added to the tank and mixed for 10 minutes. Subsequently, ingredients #1-8 (calcium D glucarate, 7 keto DHEA (ketodehydroepiandrosterone), IC3 (idole 3 carbinol), DIM (diindoylmethane), nettle root extract, agaricus biporus extract, narigin extract, and quercetin dihydrate) are added to the tank and mixed for 15 minutes until the materials dissolve completely. Natural and artificial flavor mix is then added as desired, and the components mixed for another 5 minutes. Purified water is then added to take the solution to up to 60 L volume, and the solution mixed for 10 more minutes. The solution is filtered through a Star filter into a storage tank, which is closed and labeled. At least the pH and density are tested for quality control prior to transferring the solution to a filling and packing area.

FIG. 1B is a table illustrating a resulting chemical analysis of the estrogen blocker solution. As expected, the components found correspond to the ingredients added to the solution. The proportional amounts by mass (mg) are shown for a 60 mL bottle of the estrogen blocker solution. The largest component is, of course, inert purified water. Aside from water and other "inert ingredients," the effective components from most to least in terms of mass are shown in the ingredients column. The "inert ingredients" are those components deemed ineffective for the glycogen treatment (e.g., added for flavor or consistency). Namely, from largest proportion to smallest, the effective ingredients include: calcium D glucarate, 7 keto DHEA, I3C, DIM, nettle root extract, agaricus biporus extract, narigin extract, and quercetin dehydrate.

Aside from water, there are 810 mg of the effective ingredients, and 300 mg of calcium D glucarate is more than one third of the total, and preferably about 37%. The 200 mg of 7 keto DHEA is about one quarter of the total, and preferably about 25%. The same calculations may be made for each ingredient to result in an approximate proportional amount by percent. It should be understood that the absolute amount of each ingredient may vary somewhat, such as about 10%, with the same result. That means that the amount of calcium D glucarate, for instance, may vary between 270-330 mg, while the amount of 7 keto DHEA may vary between 180-220 mg.

Directions: As a dietary supplement, take one dropper (1 ml) of the estrogen blocker solution sublingually (under the tongue) twice daily for 30 seconds and then swallow.

Glycogen Manager Solution

This extraordinary sublingual glycogen manager formula allows carbohydrates from starchy foods to pass through the body, helping to shuttle nutrients into the muscle cells, staying away from the fat cells. The scientifically tested ingredients in the glycogen manager solution support healthy insulin function by enhancing metabolism and carbohydrate uptake.

Supplement Benefits
a. Reduces Carbohydrate and Lipid Absorption
b. Decreases Calorie Absorption
c. Supports Healthy Weight Loss
d. Stimulant Free The glycogen manager solution features a unique combination of Chromium, Vanadium, Phellodendron, and Banaba—these earth elements represent and contain a broad foundation of phytochemicals that are to be used as part of a healthy diet for maintaining maximum insulin response, expediting carbohydrate metabolism. Recent studies have shed light on the potential roles of Chromium and Vanadium in maintaining proper carbohydrate and lipid metabolism at a molecular level, by binding to insulin receptors and activating the receptor's *tyrosine kinase* activity—what this means is that these compounds appear to play a role in amplifying the mechanism in insulin signaling and carbohydrate uptake. Phellodendron and Crape Myrtle (Banaba) are believed to contain certain active ingredients within the leaves that have insulin-modulating properties. Specifically, Banaba, a variety of Crape Myrtle that grows in certain parts of the world (e.g., Philippines, India, Malaysia, Australia) and contains *corosolic acid*, for which increased interest exists in relation to its potential role in treating type-2 diabetes, due to the multiple metabolic effects reported for *corosolic acid*, including stimulated glucose uptake. Research continues to show that people can obtain better results by adding increased macro/micronutrients, phytonutrients, and herbs into their daily regimen.

FIG. 2A shows a table of ingredients used to form a glycogen manager solution. The actual milligrams of each of the components for an exemplary batch are given, along with their theoretical weight. The total batch size is 60 L.

An exemplary procedure for forming the glycogen manager solution first involves adding 1000 mL purified water into a large capacity compounding tank including a mixer with nitrogen bubbling until the end of the process. Next, ingredients #6-7 and #9-10 (vegetable glycerin, polypropylene glycol, potassium benzoate, and citric acid) are added to the tank and mixed for 10 minutes. Subsequently, ingredients #1-4 (chromium (amino acid chelate), vanadium (vanadium sulfate), phellodendron extract, and Banaba extract) are added to the tank and mixed for 10 minutes until the materials dissolve completely. Natural and artificial flavor mix is then added as desired, and the components mixed for another 5 minutes. Purified water is then added to take the solution to up to 60 L volume, and the solution mixed for 10 more minutes. The solution is filtered through a Star filter into a storage tank, which is closed and labeled. At least the pH and density are tested for quality control prior to transferring the solution to a filling and packing area.

FIG. 2B is a table illustrating a resulting chemical analysis of the glycogen manager solution. As expected, the components found correspond to the ingredients added to the solution. The proportional amounts by mass (mg) are shown for a 60 mL bottle of the glycogen manager solution. The largest component is, of course, inert purified water. Aside from water and other "inert ingredients," the effective components from most to least in terms of mass are shown in the ingredients column. The "inert ingredients" are those components deemed ineffective for the glycogen treatment (e.g., added for flavor or consistency). Namely, from largest proportion to smallest, the effective ingredients include: phellodendron extract, Banaba extract, Vanadium, and Chromium.

Aside from water, there are about 380 mg of the effective ingredients, and 225 mg of phellodendron extract is more than one half of the total, and preferably about 59%. The 150 mg of Banaba extract more than one third of the total, and preferably about 39%. Vanadium and Chromium make up a very small proportion of the total ingredients, Vanadium is about 1% and preferably about 1.3%, while Chromium is less than 1% and preferably less than 0.02%. It should be understood that the absolute amount of each ingredient may vary somewhat, such as about 10%, with the same result. That means that the amount of phellodendron extract, for instance, may vary between 202-248 mg, while the amount of Banaba extract may vary between 135-165 mg.

Directions: For best results, take 15 minutes before a meal containing carbohydrates. Take a maximum of 2 droppers (2 ml) once per day under the tongue for 30 seconds and then swallow. Or you can mix with your favorite beverage. Do not exceed recommended dose and do not take more than one dose per day. It is important that you eat food within 15 minutes of using this product to avoid drop in blood sugar.

Muscle Recovery Solution

The disclosed muscle recovery solution is the most advanced, ultra-concentrated branched chain amino acid (BCAA) supplement available without a prescription. Until now, the challenge has been finding an effective delivery method to ensure a sufficient rate of absorption. The BCAA muscle recovery solution utilizes sublingual delivery (under the tongue) shuttling the purest form of L-Leucine, L Isoleucine and L-Valine directly into the bloodstream, providing absorption levels of up to 92% (up to 10 times greater than the popular powders and capsules that are broken down during the digestion process).

The BCAA muscle recovery solution is for those looking to maintain muscle mass, avoid catabolic muscle breakdown, stimulate protein synthesis, reduce fatigue, while shortening recovery time. The key to peak performance is muscle recovery. The BCAA muscle recovery solution has been engineered to enhance protein synthesis and stimulate muscular response, making it one of the most important supplements you will ever use. With no artificial coloring, no calories and no sodium, the BCAA muscle recovery solution is also used by competitive, bikini, physique and bodybuilding athletes right up to the day of the event.

FIG. 3A shows a table of ingredients used to form a muscle recovery solution. The actual milligrams of each of the components for an exemplary batch are given, along with their theoretical weight. The total batch size is 60 L.

An exemplary procedure for forming the muscle recovery solution first involves adding 300 mL purified water into a large capacity compounding tank including a mixer with nitrogen bubbling until the end of the process. Next, ingredients #5-6 and #8-9 (vegetable glycerin, polypropylene glycol, potassium benzoate, and citric acid) are added to the tank and mixed for 10 minutes. Subsequently, ingredients #1-3 (L-leucine, L-isoleucine, and L-valine) are added to the tank and mixed for 15 minutes until the materials dissolve completely. Natural and artificial flavor mix is then added as desired, and the components mixed for another 5 minutes. Purified water is then added to take the solution to up to 60 L volume, and the solution mixed for 10 more minutes. The solution is filtered through a Star filter into a storage tank, which is closed and labeled. At least the pH and density are tested for quality control prior to transferring the solution to a filling and packing area.

FIG. 3B is a table illustrating a resulting chemical analysis of the muscle recovery solution. As expected, the components found correspond to the ingredients added to the solution. The proportional amounts by mass (mg) are shown for a 60 mL bottle of the muscle recovery solution. The largest component is, of course, inert purified water. Aside from water and other "inert ingredients," the effective components from most to least in terms of mass are shown in the ingredients column. The "inert ingredients" are those components deemed ineffective for the muscle recovery (e.g., added for flavor or consistency). Namely, from largest proportion to smallest, the effective ingredients include: L-leucine, L-isoleucine, and L-valine.

Aside from water, there are about 1000 mg of the effective ingredients, and 500 mg of L-leucine is about one half of the total. L-isoleucine and L-valine both make up about one quarter of the total. It should be understood that the absolute amount of each ingredient may vary somewhat, such as about 10%, with the same result. That means that the amount of L-leucine, for instance, may vary between 450-550 mg, while the amounts of L-isoleucine and L-valine may vary between 225-275 mg.

Directions: As a dietary supplement, place one or two full droppers of the BCAA muscle recovery solution sublingual (under the tongue) 15 minutes before or immediately after your workout. On non-workout days, take one or two full droppers once daily.

While the invention has been described in its preferred embodiments, it is to be understood that the words that have been used are words of description and not of limitation. Therefore, changes may be made within the appended claims without departing from the true scope of the invention.

What is claimed is:

1. A therapeutic method of treating diabetes in a subject in need thereof, comprising:
   a) procuring a solution including at least the ingredients: purified water, phellodendron extract, Banaba extract, Vanadium, and Chromium, wherein one dropper of the solution comprises therapeutically effective amounts of each of the phellodendron extract, Banaba extract, Vanadium, and Chromium, wherein the proportional amount by mass of phellodendron extract is 59%±10%, and wherein the proportional amount by mass of Banaba extract is 39%±10%;
   b) taking one or two droppers (1 or 2 ml) of the solution sublingually for 30 seconds; and then
   c) swallowing the solution.

2. The method of claim 1, wherein the step of taking one or two droppers of the solution sublingually is done once per day.

3. The method of claim 1, further including eating food within 15 minutes of the step of swallowing.

4. The method of claim 1, wherein the largest proportional ingredient by mass aside from purified water is phellodendron extract.

5. The method of claim 4, wherein the proportional amount by mass of phellodendron extract is more than one half of the total mass of the solution.

6. The method of claim 5, wherein the proportional amount by mass of Banaba extract is more than one third of the total mass of the solution.

7. The method of claim 6, wherein the third largest proportional ingredients by mass aside from purified water is Vanadium.

8. The method of claim 7, wherein the solution further includes vegetable glycerin, polypropylene glycol, potassium benzoate, and citric acid in lesser amounts by mass than the 4 ingredients listed in claim 1.

9. The method of claim 4, wherein the second largest proportional ingredient by mass aside from purified water is Banaba extract.

10. The method of claim 9, wherein the third largest proportional ingredients by mass aside from purified water is Vanadium.

11. The method of claim 10, wherein the solution further includes vegetable glycerin, polypropylene glycol, potassium benzoate, and citric acid in lesser amounts by mass than the 4 ingredients listed in claim 1.

12. The method of claim 1, wherein of the 4 ingredients listed in claim 1 the solution includes a proportional mix by mass of 59%±10% phellodendron extract, 39%±10% Banaba extract, 1-1.3% Vanadium and less than 1% Chromium.

13. The method of claim 12, wherein the solution further includes vegetable glycerin, polypropylene glycol, potassium benzoate, and citric acid in lesser amounts by mass than the 4 ingredients listed in claim 1.

14. The method of claim 1, wherein the solution further includes vegetable glycerin, polypropylene glycol, potassium benzoate, and citric acid in lesser amounts by mass than the 4 ingredients listed in claim 1.

* * * * *